(12) United States Patent
di Palma et al.

(10) Patent No.: US 10,039,900 B2
(45) Date of Patent: Aug. 7, 2018

(54) FLUID DELIVERY AND TREATMENT DEVICE AND METHOD OF USE

(75) Inventors: Giorgio di Palma, West Valley City, UT (US); William A. Cartier, Glenville, NY (US); William M. Appling, Granville, NY (US)

(73) Assignee: AngioDynamics, Inc., Latham, NY (US)

( * ) Notice: Subject to any disclaimer, the term of this patent is extended or adjusted under 35 U.S.C. 154(b) by 230 days.

(21) Appl. No.: 13/226,538

(22) Filed: Sep. 7, 2011

(65) Prior Publication Data

US 2012/0059309 A1 Mar. 8, 2012

Related U.S. Application Data

(60) Provisional application No. 61/380,513, filed on Sep. 7, 2010, provisional application No. 61/383,971, filed
(Continued)

(51) Int. Cl.
| | |
|---|---|
| *A61M 25/00* | (2006.01) |
| *A61B 17/22* | (2006.01) |
| *A61B 17/221* | (2006.01) |
| *A61B 17/12* | (2006.01) |
| *A61M 5/142* | (2006.01) |

(Continued)

(52) U.S. Cl.
CPC ... *A61M 25/0074* (2013.01); *A61B 17/12186* (2013.01); *A61B 17/22* (2013.01); *A61B 17/221* (2013.01); *A61M 5/142* (2013.01); *A61M 5/158* (2013.01); *A61M 25/007* (2013.01); *A61B 2017/00853* (2013.01); *A61B 2017/22002* (2013.01); *A61B 2017/2212* (2013.01); *A61B 2017/22034* (2013.01); *A61B 2017/22082* (2013.01); *A61B 2017/22084* (2013.01); *A61M 2025/109* (2013.01)

(58) Field of Classification Search
CPC ................ A61M 25/104; A61M 25/10; A61M 25/1011; A61M 25/0113; A61F 2/013
USPC .......... 604/96.01, 101.01, 159; 606/200, 108
See application file for complete search history.

(56) References Cited

U.S. PATENT DOCUMENTS

| | | | |
|---|---|---|---|
| 3,831,587 A | | 8/1974 | Boyd |
| 4,046,150 A | * | 9/1977 | Schwartz et al. ............. 606/127 |

(Continued)

FOREIGN PATENT DOCUMENTS

| | | |
|---|---|---|
| WO | WO2005079678 | 9/2005 |
| WO | VO2011144336 | 11/2011 |

OTHER PUBLICATIONS

Nael, et al, Endovascular Mangement of Central Thoracic Veno-Occlusive Disease in Hemodialysis Patients, J Vasc Interv Radiol 2009, pp. 46-51.

(Continued)

*Primary Examiner* — Bhisma Mehta
*Assistant Examiner* — Matthew A Engel
(74) *Attorney, Agent, or Firm* — Zachary F. Madonna, Esq.

(57) ABSTRACT

A medical device system is provided herein which has an elongated, flexible hollow member with an expandable infusion segment attached at the most distal end of the device. The device has a plurality of fluid infusion ports on the expandable infusion segment for delivering an intended fluid to a target site in a body lumen. Additionally, a method is provided herein for infusing an intended fluid to a target site within a body lumen.

10 Claims, 16 Drawing Sheets

Related U.S. Application Data on Sep. 17, 2010, provisional application No. 61/388,669, filed on Oct. 1, 2010.

(51) Int. Cl.
*A61M 5/158* (2006.01)
*A61B 17/00* (2006.01)
*A61M 25/10* (2013.01)

(56) References Cited

U.S. PATENT DOCUMENTS

| | | | |
|---|---|---|---|
| 4,273,128 A * | 6/1981 | Lary | 606/159 |
| 4,437,856 A * | 3/1984 | Valli | 604/29 |
| 4,445,509 A | 5/1984 | Auth | |
| 4,469,100 A | 9/1984 | Hardwick | |
| 4,646,736 A | 3/1987 | Auth | |
| 4,664,112 A | 5/1987 | Kensey et al. | |
| 4,671,796 A * | 6/1987 | Groshong | A61M 25/00 604/170.01 |
| 4,681,564 A * | 7/1987 | Landreneau | 604/128 |
| 4,693,243 A * | 9/1987 | Buras | 128/207.15 |
| 4,696,667 A | 9/1987 | Masch | |
| 4,729,763 A | 3/1988 | Henrie | |
| 4,747,821 A | 5/1988 | Kensey et al. | |
| 4,749,376 A | 6/1988 | Kensey et al. | |
| 4,790,812 A * | 12/1988 | Hawkins et al. | 604/22 |
| 4,857,045 A | 8/1989 | Rydell | |
| 4,857,046 A | 8/1989 | Stevens et al. | |
| 4,886,061 A * | 12/1989 | Fischell et al. | 606/159 |
| 4,895,166 A | 1/1990 | Farr et al. | |
| 4,895,560 A * | 1/1990 | Papantonakos | 604/22 |
| 4,921,478 A | 5/1990 | Solano et al. | |
| 4,990,134 A | 2/1991 | Auth | |
| 4,990,151 A | 2/1991 | Wallsten | |
| 5,011,488 A * | 4/1991 | Ginsburg | 606/159 |
| 5,019,089 A | 5/1991 | Farr | |
| 5,030,201 A | 7/1991 | Palestrant | |
| 5,074,841 A | 12/1991 | Ademovic et al. | |
| 5,084,052 A | 1/1992 | Jacobs | |
| 5,092,877 A * | 3/1992 | Pinchuk | 128/898 |
| 5,098,440 A | 3/1992 | Hillstead | |
| 5,100,423 A * | 3/1992 | Fearnot | 606/159 |
| 5,114,399 A | 5/1992 | Kovalcheck | |
| 5,158,564 A * | 10/1992 | Schnepp-Pesch et al. | 606/159 |
| 5,226,909 A | 7/1993 | Evans et al. | |
| 5,257,974 A * | 11/1993 | Cox | 604/103.05 |
| 5,273,526 A | 12/1993 | Dance et al. | |
| 5,306,250 A * | 4/1994 | March et al. | 604/104 |
| 5,334,208 A | 8/1994 | Soehendra et al. | |
| 5,423,799 A | 6/1995 | Shiu | |
| 5,464,408 A | 11/1995 | Duc | |
| 5,474,563 A | 12/1995 | Myler et al. | |
| 5,490,859 A * | 2/1996 | Mische et al. | 606/159 |
| 5,520,697 A | 5/1996 | Lindenberg et al. | |
| 5,540,707 A | 7/1996 | Ressemann et al. | |
| 5,569,275 A | 10/1996 | Kotula et al. | |
| 5,571,086 A * | 11/1996 | Kaplan et al. | 604/96.01 |
| 5,628,746 A * | 5/1997 | Clayman | 606/45 |
| 5,632,755 A | 5/1997 | Nordgren et al. | |
| 5,643,309 A | 7/1997 | Myler et al. | |
| 5,653,684 A | 8/1997 | Laptewicz et al. | |
| 5,733,302 A | 3/1998 | Myler et al. | |
| 5,772,629 A * | 6/1998 | Kaplan | 604/508 |
| 5,776,141 A * | 7/1998 | Klein et al. | 623/1.11 |
| 5,785,715 A | 7/1998 | Schatz | |
| 5,843,103 A | 12/1998 | Wulfman | |
| 5,868,753 A | 2/1999 | Schatz | |
| 5,873,882 A | 2/1999 | Straub et al. | |
| 5,910,144 A | 6/1999 | Hayashi | |
| 5,941,895 A | 8/1999 | Myler et al. | |
| 6,001,112 A | 12/1999 | Taylor | |
| 6,106,531 A | 8/2000 | Schatz | |
| 6,187,016 B1 | 2/2001 | Hedges et al. | |
| 6,203,537 B1 | 3/2001 | Adrian | |
| 6,206,898 B1 | 3/2001 | Honeycutt et al. | |
| 6,241,738 B1 | 6/2001 | Dereume | |
| 6,280,413 B1 | 8/2001 | Clark et al. | |
| 6,280,464 B1 | 8/2001 | Hayashi | |
| 6,283,940 B1 * | 9/2001 | Mulholland | 604/96.01 |
| 6,394,978 B1 * | 5/2002 | Boyle et al. | 604/103.06 |
| 6,443,966 B1 | 9/2002 | Shiu | |
| 6,451,036 B1 | 9/2002 | Heitzmann et al. | |
| 6,454,775 B1 | 9/2002 | Demarais et al. | |
| 6,454,779 B1 | 9/2002 | Taylor | |
| 6,508,782 B1 | 1/2003 | Evans et al. | |
| 6,547,754 B1 | 4/2003 | Evans et al. | |
| 6,569,181 B1 | 5/2003 | Burns | |
| 6,582,396 B1 | 6/2003 | Parodi | |
| 6,602,264 B1 | 8/2003 | McGuckin, Jr. | |
| 6,660,014 B2 | 12/2003 | Demarais et al. | |
| 6,666,874 B2 | 12/2003 | Heitzmann et al. | |
| 6,676,692 B2 | 1/2004 | Rabkin et al. | |
| 6,679,893 B1 | 1/2004 | Tran | |
| 6,702,830 B1 | 3/2004 | Demarais et al. | |
| 6,719,717 B1 | 4/2004 | Johnson et al. | |
| 6,749,619 B2 * | 6/2004 | Ouriel et al. | 606/200 |
| 6,802,846 B2 | 10/2004 | Hauschild et al. | |
| 6,837,901 B2 | 1/2005 | Rabkin et al. | |
| 6,945,977 B2 | 9/2005 | Demarais et al. | |
| 7,014,913 B2 * | 3/2006 | Pacetti | 428/212 |
| 7,108,704 B2 * | 9/2006 | Trerotola | 606/159 |
| 7,153,320 B2 | 12/2006 | Euteneuer et al. | |
| 7,172,610 B2 | 2/2007 | Heitzmann et al. | |
| 7,235,088 B2 | 6/2007 | Pintor et al. | |
| 7,258,696 B2 | 8/2007 | Rabkin et al. | |
| 7,351,255 B2 * | 4/2008 | Andreas | 623/1.12 |
| 7,479,147 B2 | 1/2009 | Honeycutt et al. | |
| 7,655,016 B2 | 2/2010 | Demarais et al. | |
| 7,771,445 B2 | 8/2010 | Heitzmann et al. | |
| 7,842,010 B2 | 11/2010 | Bonnette et al. | |
| 7,842,055 B2 | 11/2010 | Pintor et al. | |
| 7,862,575 B2 * | 1/2011 | Tal | 606/159 |
| 7,879,022 B2 | 2/2011 | Bonnette et al. | |
| 7,892,273 B2 * | 2/2011 | George et al. | 623/1.11 |
| 7,912,531 B1 * | 3/2011 | Chiu et al. | 600/423 |
| 8,034,095 B2 | 10/2011 | Randolph et al. | |
| 8,038,704 B2 | 10/2011 | Sherburne | |
| 8,075,510 B2 | 12/2011 | Aklog et al. | |
| 8,167,903 B2 | 5/2012 | Hardert et al. | |
| 8,317,859 B2 * | 11/2012 | Snow et al. | 623/6.12 |
| 8,470,016 B2 | 6/2013 | Sherburne | |
| 8,734,374 B2 | 5/2014 | Aklog et al. | |
| 8,828,073 B2 | 9/2014 | Sherburne | |
| 8,945,141 B2 | 2/2015 | Cahill | |
| 9,351,861 B2 | 5/2016 | Sherburne | |
| 2001/0011179 A1 | 8/2001 | Adams | |
| 2002/0010487 A1 | 1/2002 | Evans et al. | |
| 2002/0072764 A1 | 6/2002 | Sepetka et al. | |
| 2002/0120277 A1 | 8/2002 | Hauschild et al. | |
| 2002/0143387 A1 | 10/2002 | Soetikno et al. | |
| 2002/0151918 A1 | 10/2002 | Lafontaine et al. | |
| 2002/0161377 A1 | 10/2002 | Rabkin | |
| 2002/0161427 A1 | 10/2002 | Rabkin et al. | |
| 2002/0188276 A1 | 12/2002 | Evans et al. | |
| 2003/0023204 A1 | 1/2003 | Vo et al. | |
| 2003/0055445 A1 | 3/2003 | Evans et al. | |
| 2003/0195537 A1 | 10/2003 | Dubrul et al. | |
| 2003/0199890 A1 | 10/2003 | Dubrul et al. | |
| 2003/0236533 A1 | 12/2003 | Wilson et al. | |
| 2004/0082962 A1 | 4/2004 | Demarais et al. | |
| 2004/0147939 A1 | 7/2004 | Rabkin et al. | |
| 2004/0181237 A1 | 9/2004 | Forde et al. | |
| 2004/0210298 A1 | 10/2004 | Rabkin et al. | |
| 2005/0004594 A1 | 1/2005 | Nool et al. | |
| 2005/0080431 A1 | 4/2005 | Levine et al. | |
| 2005/0080480 A1 | 4/2005 | Bolea et al. | |
| 2006/0189930 A1 | 8/2006 | Lary et al. | |
| 2006/0200191 A1 | 9/2006 | Zadno-Azizi | |
| 2007/0027520 A1 | 2/2007 | Sherburne | |
| 2007/0118072 A1 | 5/2007 | Nash | |
| 2008/0033482 A1 | 2/2008 | Kusleika | |
| 2008/0249558 A1 | 10/2008 | Cahill | |
| 2009/0099581 A1 | 4/2009 | Kim et al. | |
| 2009/0222035 A1 | 9/2009 | Schneiderman | |

(56) References Cited

U.S. PATENT DOCUMENTS

| | | |
|---|---|---|
| 2009/0292307 A1 | 11/2009 | Razack |
| 2009/0306702 A1* | 12/2009 | Miloslavski et al. ......... 606/200 |
| 2010/0057184 A1 | 3/2010 | Randolph et al. |
| 2011/0190806 A1 | 8/2011 | Wittens |
| 2012/0016455 A1 | 1/2012 | Sherburne |
| 2012/0059309 A1 | 3/2012 | di Palma et al. |
| 2013/0289694 A1 | 10/2013 | Sherburne |
| 2014/0350591 A1 | 11/2014 | Sherburne |
| 2015/0127044 A1 | 5/2015 | Cahill |

OTHER PUBLICATIONS

Valji, et al, Pulsed-Spray Thrombolysis of Arterial and Bypass Graft Occlusion, American Roentgen Ray Society, pp. 617-621 (Mar. 1991).

International Search Report PCT-NL-08-050399 ISR dated Feb. 13, 2009.

\* cited by examiner

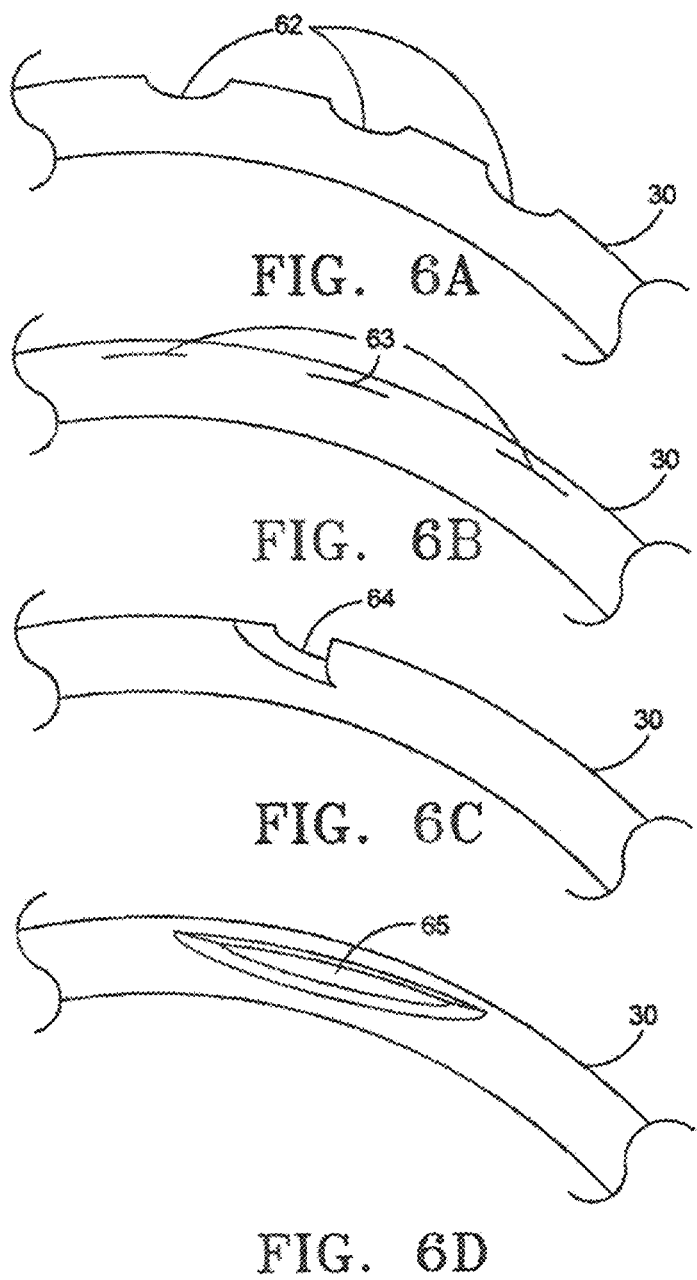

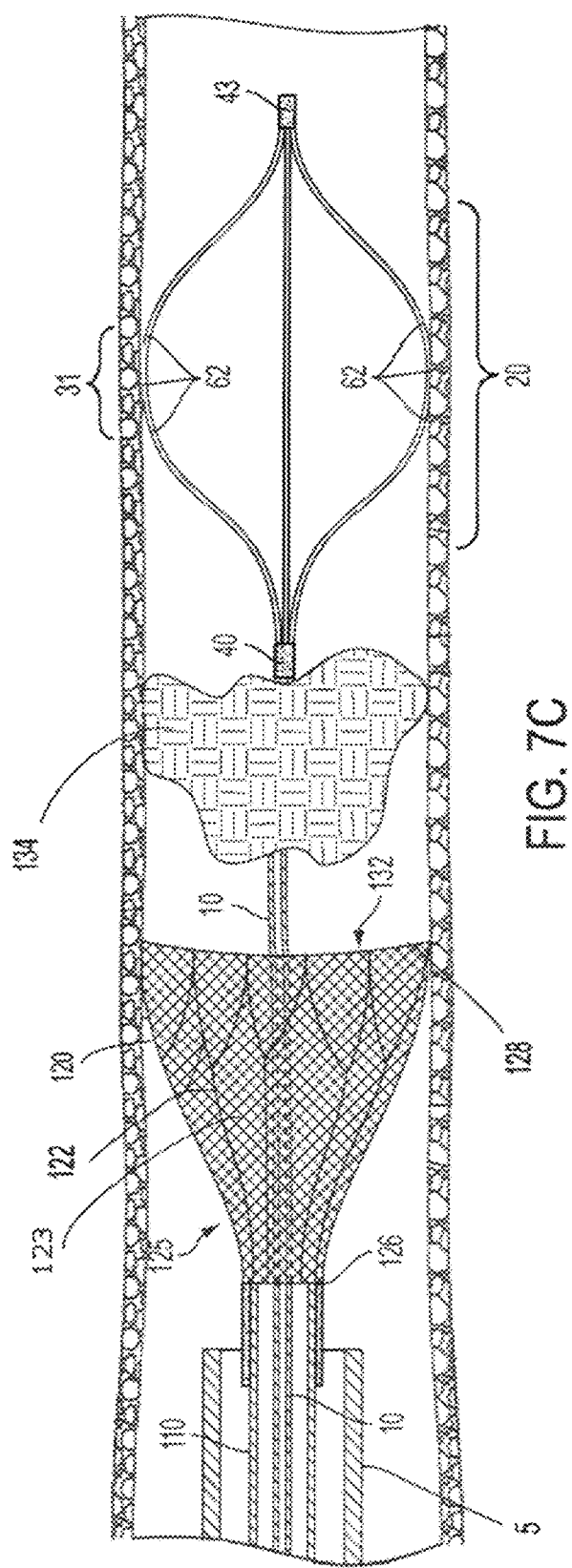

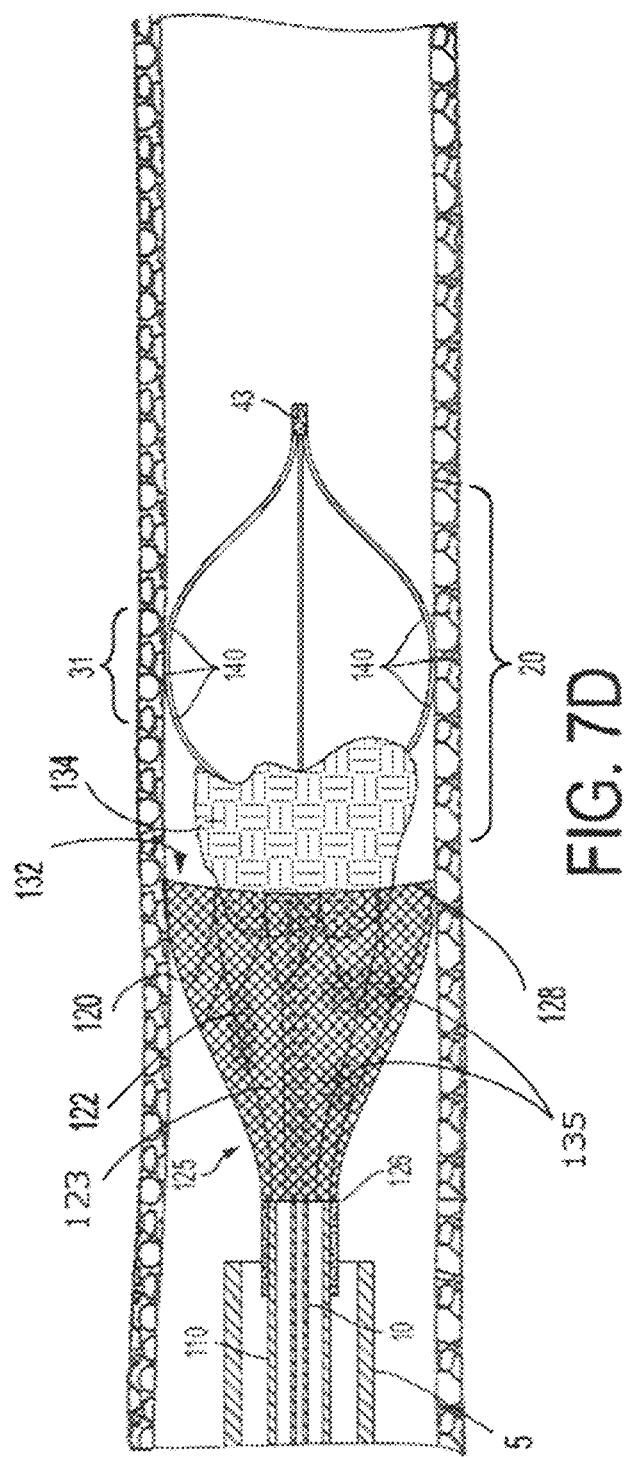

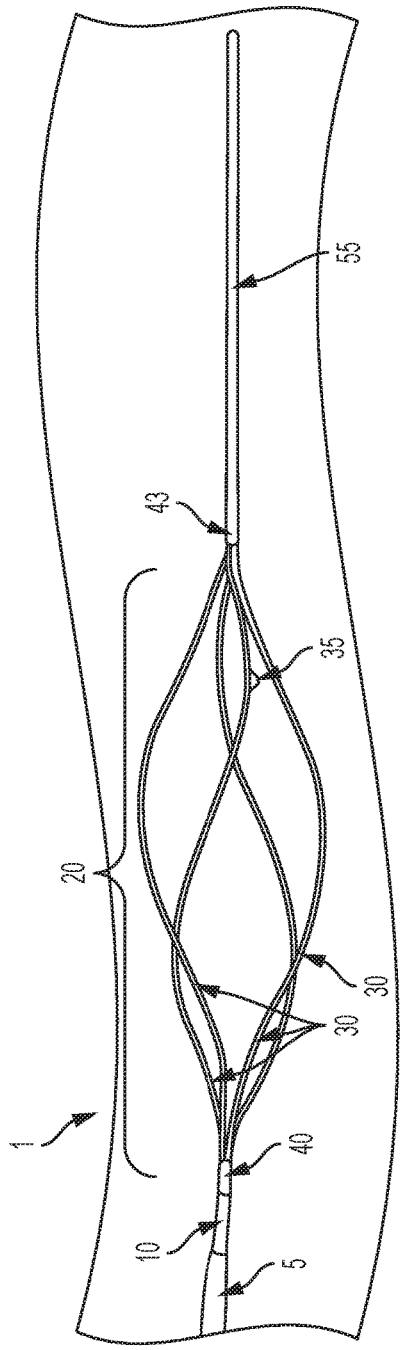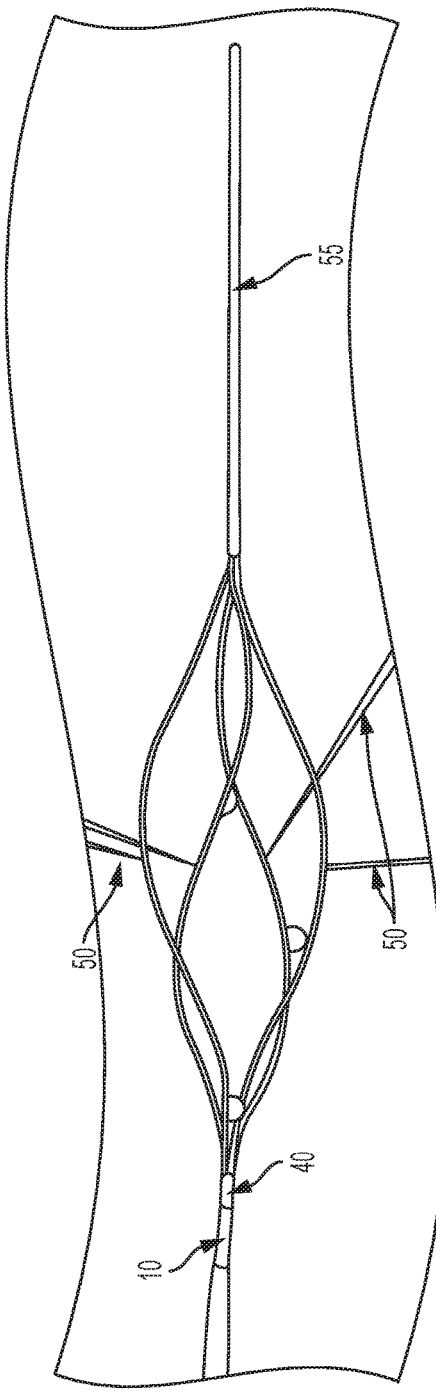

FLUID DELIVERY AND TREATMENT DEVICE AND METHOD OF USE

CROSS-REFERENCE TO RELATED APPLICATIONS

This application claims priority to U.S. provisional application No. 61/380,513 filed on Sep. 7, 2010, U.S. provisional application No. 61/383,971 filed on Sep. 17, 2010, and U.S. provisional application No. 61/388,669 filed on Oct. 1, 2010, all of which are incorporated herein by reference in their entireties.

TECHNICAL FIELD

The present invention relates generally to devices for delivering a fluid, drugs or other medical preparations to a site within a patient's body. More specifically, the invention relates to an elongated device that delivers fluid, drugs or other medical preparations to a site within a lumen of a blood vessel or another cavity or lumen within a patient's body to treat the targeted area. A method of use is also disclosed.

BACKGROUND OF THE INVENTION

Devices for delivering fluid to a target site within a human lumen are generally known. For example, it is known to use a catheter for infusing fluid to a target site within a blood vessel for treating issues such as thrombosis or varicose veins. However, delivering fluid from a catheter to a target site such as a thrombus mass requires waiting a long time for the fluid to disseminate through the entire clot. Further, when large amounts of fluid drugs are introduced to a target site such as a clot or inner vessel wall, they can enter the bloodstream once blood flow is restored, causing adverse effects. Drug delivery balloons are generally known, however they take up volume in the device and are known to force clots against the wall of the vein.

SUMMARY

The present invention is directed to a device and method of delivering fluid to a target site and treating a target site within a human body. The device and method are particularly useful for a method of treating a vessel and a method of treating thrombosis.

In one embodiment, a method of treating a hollow anatomical structure within a human body includes inserting a catheter attached to an expandable infusion segment into the hollow anatomical structure, where the expandable infusion segment multiple expandable arms and multiple fluid channels, and where at least one of the plurality of fluid channels is in fluid communication with at least one infusion port. The expandable infusion segment is advanced to a target site within the hollow anatomical structure and expanded to a first diameter. A first amount of fluid is delivered through at least one infusion port to an inner wall of the hollow anatomical structure and the expandable infusion segment is adjusted to a second diameter, where the second diameter is less than the first diameter. A second amount of fluid is delivered through the at least one infusion port to the inner wall of the hollow anatomical structure.

In another embodiment, a method of treating a varicose vein using schelerosant within a human body includes inserting a catheter attached to an expandable infusion segment into the vein, where the expandable infusion segment comprises multiple expandable arms and a plurality of fluid channels, and where at least one of the multiple fluid channels is in fluid communication with at least one infusion port. The expandable infusion segment is advanced to a target site within the vein and expanded to a first diameter. Fluid is then delivered fluid through at least one infusion port while simultaneously moving the expandable infusion segment along a path of the vein.

In another embodiment, method of treating a thrombus mass within a human body includes inserting a catheter attached to an expandable infusion segment into the human body, where the expandable infusion segment comprises a plurality of expandable arms and a plurality of fluid channels, and where at least one of the plurality of fluid channels is in fluid communication with at least one infusion port. The expandable infusion segment is advanced to the thrombus mass and a first amount of fluid is delivered through at least one infusion port to the thrombus mass while the expandable infusion segment is at a first diameter. The expandable infusion segment is advanced to a second diameter, wherein the second diameter is different than the first diameter, and a second amount of fluid is delivered through the at least one infusion port to the thrombus mass.

The fluid delivery and treatment device according to the present invention allows a user to deliver a desired fluid drug or treatment to the outermost edges of a clot, or directly to an inner vessel wall. In one example, this manner of treatment is desired in the treatment of thrombosis because it breaks the clot away from the inner vessel wall. When remnants of a blood clot remain attached an inner vessel wall, blood flow may be obstructed, which can facilitate the formation of a new clot at the site of the obstruction. Therefore, removing the entire clot from the inner vessel wall will remove the obstruction and help to prevent the clot from reforming. In another example, this manner of treatment is desired in sclerotherapy for treating varicose veins because fluid drugs can be applied directly to the inner vessel wall. The device also allows a user to deliver a desired drug to an inner core of a clot, facilitating the dissemination of the fluid through the clot. In addition, the amount of drug necessary for treatment is minimized as infusion accuracy becomes more precise, further limiting the risk of fluid drugs traveling through the flowing blood to unintended target areas. In addition to controlling the direction and location of the delivered fluid, the fluid delivery and treatment device allows the user to control the pressure of the fluid, the flow rate, and also the manner in which the fluid is delivered. The elements of the device can also be shaped to aid mechanical abrasion of a thrombus or inner vessel wall.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 6A-6D are enlarged partial plan views of various embodiments of the infusion ports positioned along an infusion arm.

FIGS. 7A-7E depict the fluid delivery device within a vessel segment. FIG. 7A illustrates the device prior to deployment of the infusion segment. FIG. 7B illustrates the device after expansion of the infusion segment. FIG. 7C illustrates an alternative embodiment of the fluid delivery device having an expandable capture sheath. FIG. 7D illustrates an infusion segment dragging a thrombus mass and thrombus debris into an expandable capture sheath. FIG. 7E illustrates the device with the procedure sheath partially retracted.

FIG. 9 is photographic image of a prototype of the current invention in a deployed position.

FIG. 10 is a photographic image of prototype of FIG. 9 illustrating jets of fluid exiting from infusion ports.

DETAILED DESCRIPTION OF THE INVENTION

Figure 1:
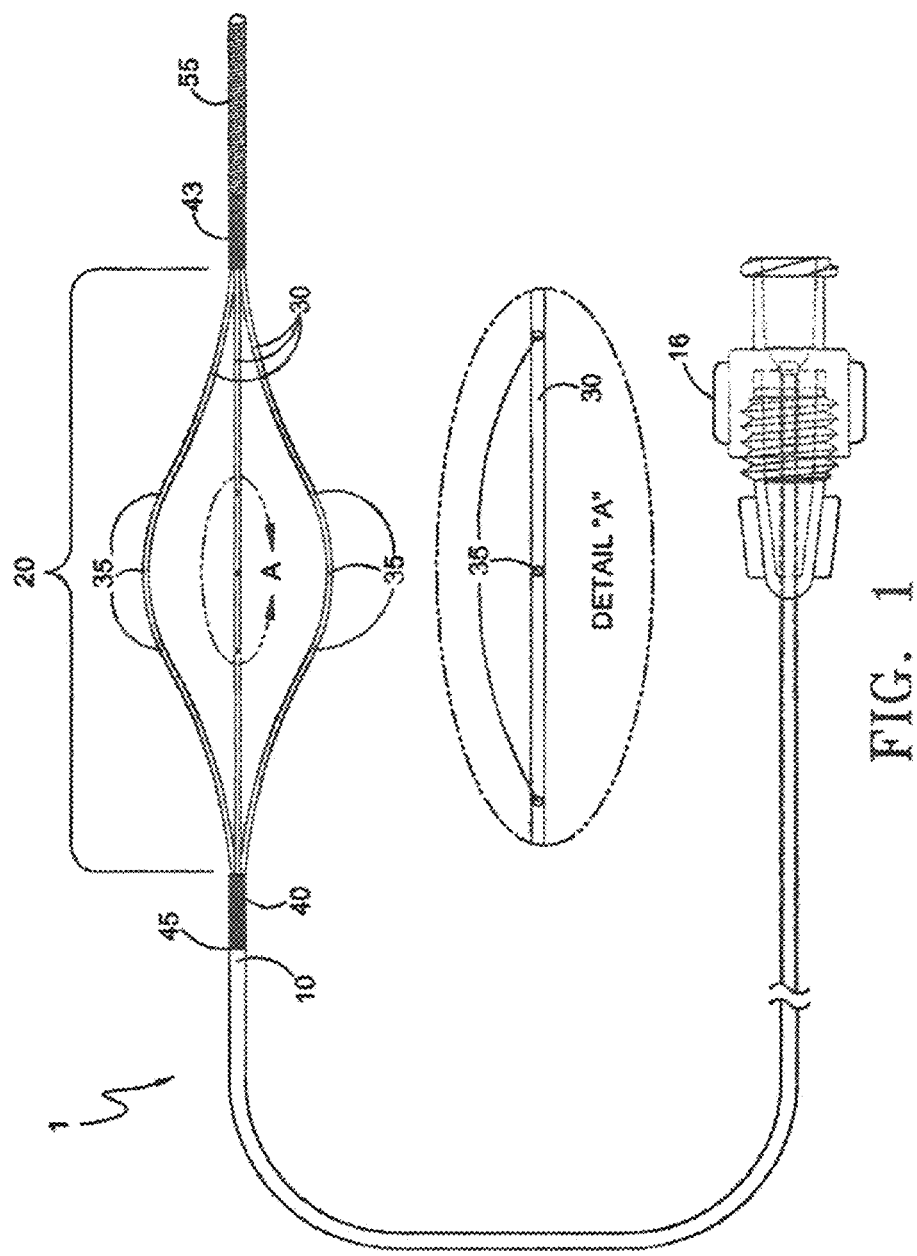
FIG. 1 is plan view of a fluid delivery device with the infusion segment in an expanded position according to an exemplary embodiment the present invention.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a fluid delivery and treatment device intended for the delivery of fluids within an anatomic lumen or cavity and treatment of the desired region.

Referring to FIG. 1, a fluid delivery and treatment device 1 for introducing material into the vascular system or other tubular anatomical structure is provided herein. Device 1, shown in an expanded or deployed state, includes a proximal hub 16, an elongated hollow member 10, an expandable infusion segment 20 and a leading flexible tip 55. The expandable infusion segment 20 is comprised of a plurality of infusion arms 30 which each contain at least one infusion port 35 as shown in Detail "A". The expandable infusion segment 20 is attached to an elongated shaft 10 by a proximal collar 40, and to the leading flexible tip 55 by a distal collar 43.

The proximal-most end of the hollow member 10 may be fitted with a removable hub 16 to allow attachment of an injection source or device. The hub 16 can also be removed to allow the device 1 to be inserted through another treatment device. For example, the hub 16 may be removed so that a catheter can be back loaded over the proximal most end of the device, such as for the subsequent placement of another type of interventional device.

Figure 2A:
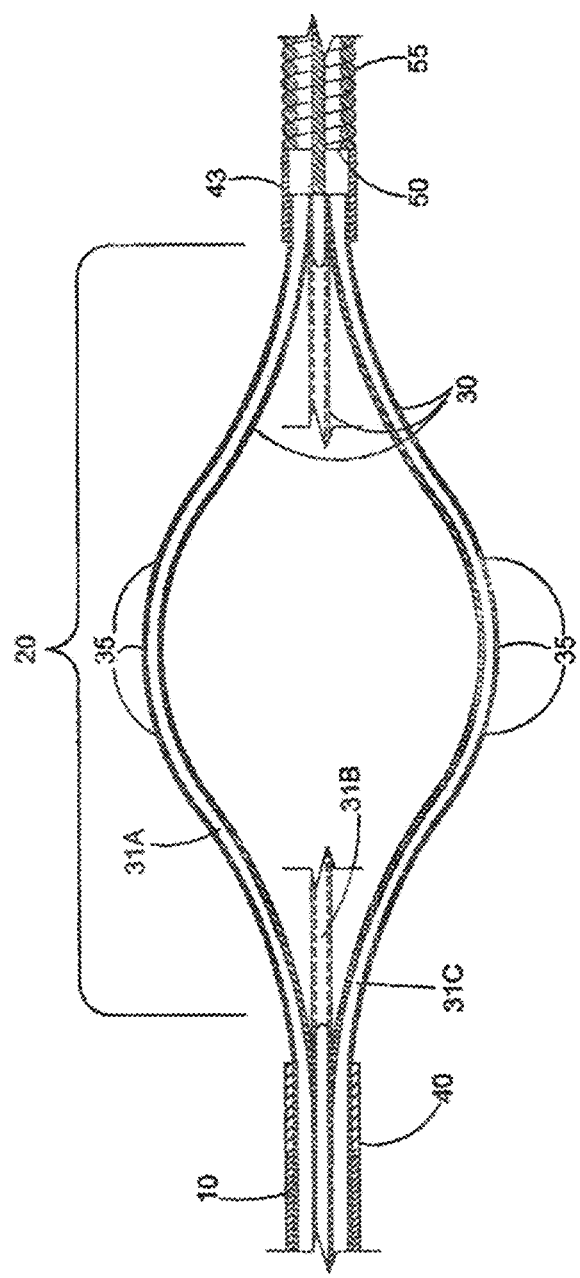
FIG. 2A is a partial enlarged cross-sectional view of the expanded infusion segment.
Figure 2B:
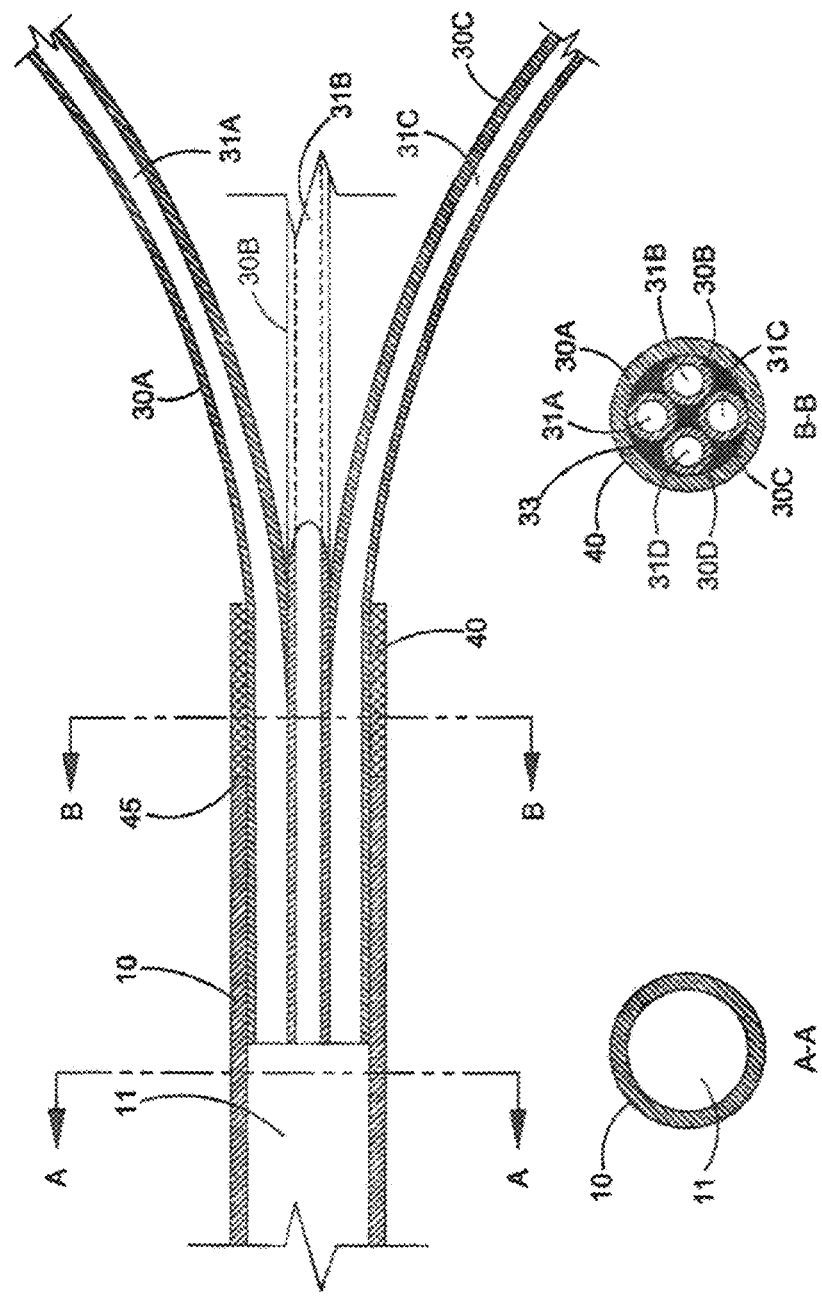
FIG. 2B is a partial enlarged cross-sectional view of the proximal portion of the expanded infusion segment.

FIG. 2A depicts a partial enlarged longitudinal cross-sectional view of the expanded infusion segment. FIG. 2B illustrates a single lumen 11 of the elongated hollow member 10 transitioning into a plurality of dedicated infusion arm lumens or channels 31A, 31B, 31C and 31D (lumen 31D is not visible in FIG. 2A or 2B). The elongated hollow member 10 is attached to the proximal collar 40 which extends distally over and coaxially surrounds the plurality of infusion arms 30A-D as shown in cross-section B-B of FIG. 2B. The elongated hollow member 10 terminates at location 45 where it abuts against the proximal end of the proximal collar 40. As shown in cross-section B-B, the proximal collar 40 extends distally over and coaxially surrounds the plurality of infusion arms 30A-D. The proximal sections of arms 30A-D are held in place within the shaft 10 and the proximal collar 40 by an adhesive or bonding agent 33. Other techniques known in the art such as welding or overmolding may be used.

Figure 2C:
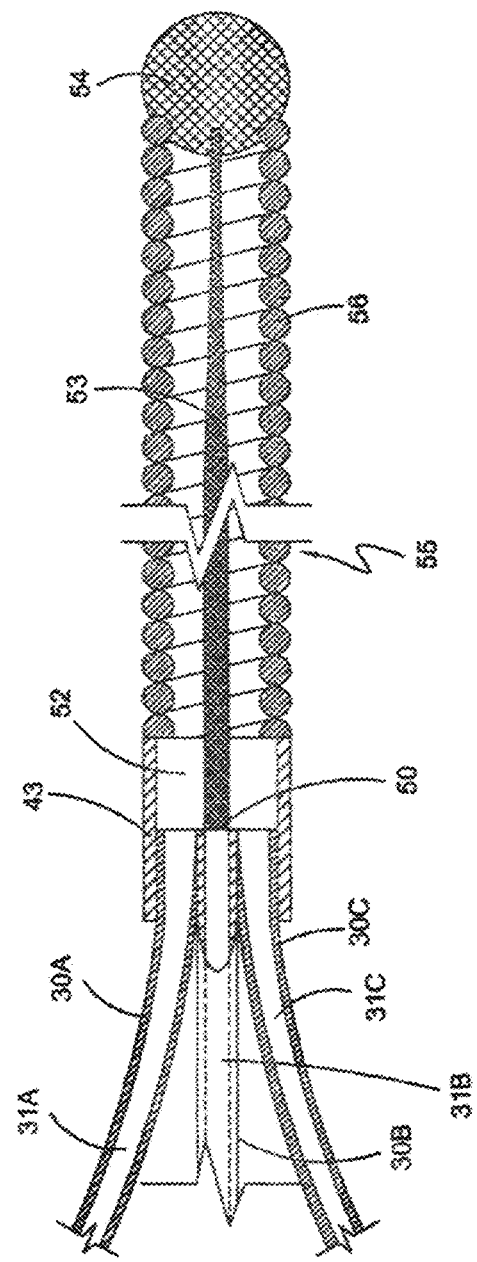
FIG. 2C is a partial enlarged cross-sectional view of the distal portion of the expanded infusion segment.

FIG. 2C depicts a partial enlarged longitudinal cross-sectional view of the distal portion of the expanded infusion segment 20 with the leading flexible tip 55. The dedicated infusion arms 30A-D extend distally in a radially inward direction to meet the distal collar 43. Each infusion arm 30A-D is held in place by the distal collar 43 which coaxially surrounds the plurality of arms. Each infusion lumen 31A-D terminates at the plug 52. The plug 52 also houses an internal mandrel wire 53 which extends distally through the flexible tip 55 to a weld ball 54. A spring coil 56, which is positioned in a spiral fashion around the mandrel wire 53, provides a leading "floppy" tip as is known in the art. The flexible tip 55 facilitates tracking and advancement of the device 1 through the vessel or alternatively through the lumen of a catheter or other treatment device. In one embodiment, the flexible tip 55 is approximately 1-2 centimeters in length. The coil portion and distal end weld ball may define an outer diameter of between 0.014"-0.045". Alternatively, an embodiment may be built on a catheter platform between 3 French (0.039") to 20 French (0.262").

In this first embodiment, the device is sized appropriately so that it can be inserted into a procedural catheter or sheath. As an example, the hollow member 10 may be comprised of a flexible hollow wire material which has an outer diameter of approximately 0.034"-0.037". Furthermore, the radius of the expandable infusion segment 20 in its compressed state would be the same size as the outer diameter of the hollow member, approximately 0.034"-0.037". Having the hollow member 10 and the expandable infusion segment 20 in its compressed state of approximately 0.034"-0.037" allows for advancement through a standard 0.035"-0.038" catheter lumen. These ranges are merely examples to show that according to this embodiment, the outer diameter of the hollow member 10 will be less than the procedure catheter or sheath lumen which in turn allows for proper advancement of the device 1.

In operation, the infusion device 1 may be introduced into the target vessel or other anatomical site using minimally invasive access techniques known in the art. In one embodiment, the device is comprised of a medical grade metal such as Nitinol and dimensioned with an outer diameter of 0.035" so as to be capable of being introduced through a standard catheter. The leading flexible tip 55 facilitates advancement of the device through the vessel to the targeted treatment site. Once positioned, a constraining sleeve or catheter (not shown) is retracted to deploy the infusion segment in an expanded position as shown in FIG. 1. Medicinal fluid may then be introduced through hub 16 (FIG. 1). The fluid travels distally through the single lumen 11 of elongated hollow member 10 to the expanded infusion segment 20, where fluid exits through the plurality of ports 35 into the targeted treatment site. Specifically, fluid flows through the single lumen 11 and is directed into the dedicated lumens 31A-D of expanded infusion arms 30A-D. Fluid flows distally through each dedicated arm lumen exiting through the plurality of ports 35 so as to come in contact with a targeted thrombus, inner vessel wall, or other treatment target.

In another aspect of the invention, the infusion segment is not self-expanding when unconstrained by a sleeve, but rather is mechanically adjustable to various diameters. For example, a tension wire extending through the shaft from the hub and connected to a distal portion of the infusion segment may be used to adjust the deployment diameter of the infusion segment. The operator may mechanically expand the infusion segment to a desired diameter before infusing fluid. In yet another embodiment, a self-expanding design is contemplated using a sleeve or catheter to control the expanded diameter of the infusion segment. The diameter may be adjusted by the operator using a sleeve or catheter which may be advanced over and retracted from the infusion segment to adjust the outer diameter.

In one example of treating a thrombus, the device is advanced to the treatment area and the infusion segment is positioned within the thrombus mass. Using the tension wire or other mechanical adjustment means, the infusion segment is expanded to a small diameter, and fluid is dispersed through the exit ports into the inner core of the thrombus mass. In some instances, fluid may be delivered without expanding the infusion segment at all. Subsequent adjustment of the infusion segment to a larger diameter followed by re-infusion of fluid through the ports will cause the agent to be dispersed further through the clot mass. Using this incremental expansion method, the therapeutic agent may be dispersed homogenously throughout the clot mass, ultimately reaching the vessel wall. Alternatively, the infusion segment may be positioned within the clot and then expanded to a maximum profile or diameter for the infusion of the lytic agent to the outer clot mass first. The infusion segment may then be incrementally decreased in diameter, working its way into the inner core of the clot mass.

In one aspect of the invention, the infusion delivery device may also be used to mechanically disrupt and/or abrade the targeted tissue by manipulating the expanded infusion segment. The device may be rotated around its longitudinal axis and/or repeatedly advanced and retracted through the targeted area to macerate or abrade the thrombus, and to further disperse the medicinal agent within the thrombus mass.

In yet another embodiment, the infusion device can be used to deliver a sclerosant agent for the treatment of varicose veins. Sclerosant agents damage the vessel wall, causing the vein to collapse. One example of such an agent is Sotradecol® sclerosant. When treating a vein with sclerosant, it is optimal to deliver the drug directly to the vessel wall itself rather than directing the fluid into the vessel lumen and blood stream. Sclerosant diluted by blood will be washed away and ineffective in damaging the vein wall. In one method of the current invention, the infusion device may be used to deliver sclerosant directly to the vessel wall, thereby minimizing the amount of drug that is diluted by the blood flow. The infusion device is placed at a desired treatment location within the vein. The infusion segment is then expanded to its maximum profile or diameter causing the infusion arms to contact the inner wall. Fluid delivered through the device will exit from the infusion ports located on the expanded arms and come into direct contact with the vessel wall, thereby maximizing the amount of drug delivered to the vessel wall, and reducing the total fluid volume required to achieve a successful treatment. Optionally, as the vessel collapses, or as the vessel anatomy decreases in diameter, the outer diameter of the infusion segment may be reduced to accommodate the smaller vessel diameter and the drug delivery may be continued. This method may be repeated to cover longer treatment lengths of veins by segmental treatment and subsequent repositioning of the device along another segment of the vein. Alternatively, a continual pull back method may be used to deliver the drug along the course of a long vein segment. Since the infusion segment is expandable and collapsible, it can expand and collapse, maintaining contact with the inner vessel wall, based on the variable diameter of the vessel anatomy at a particular location along the course of the vein segment.

Figure 3:
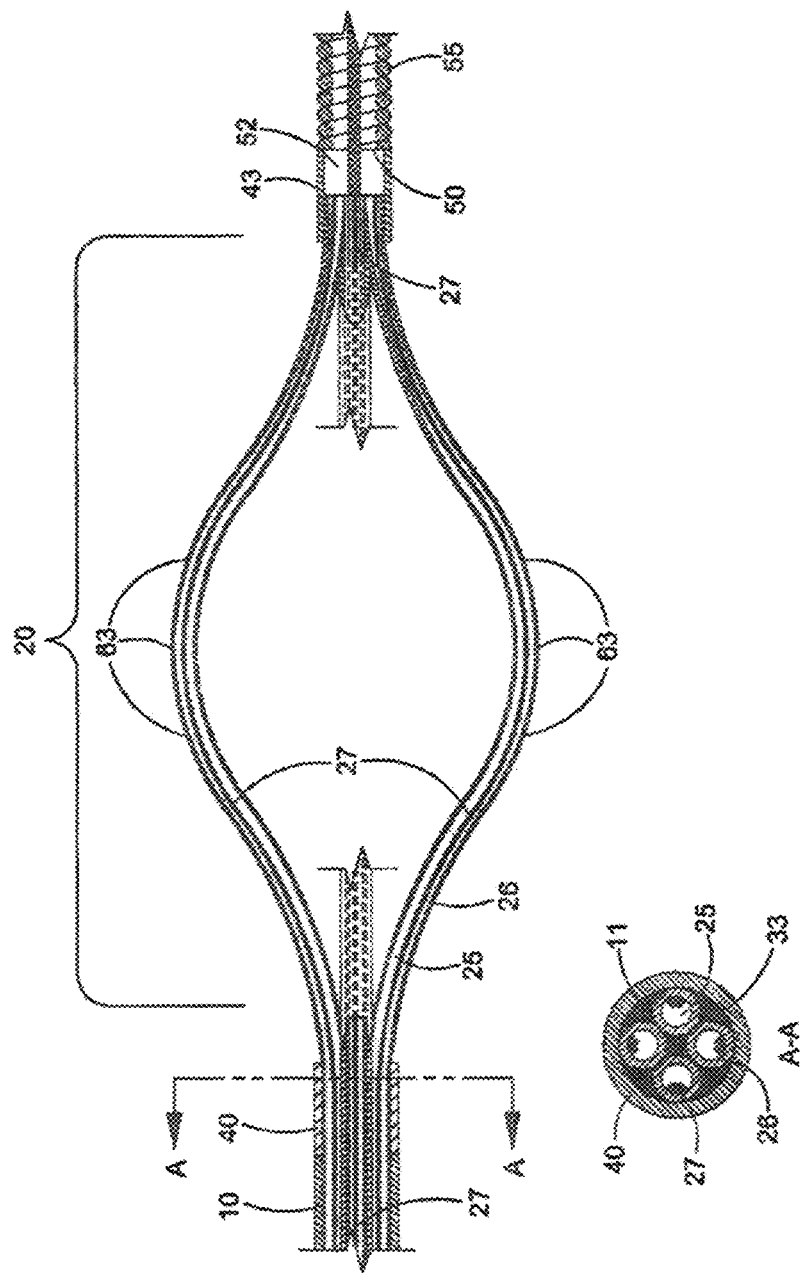
FIG. 3 is a partial cross-sectional view of an alternative embodiment of the fluid delivery device with the infusion segment in an expanded position according to the present invention.

Referring now to FIG. 3, an alternative embodiment of the current invention is shown in an enlarged partial cross-sectional view. In this embodiment, the infusion device 1 is comprised mainly of a flexible polymer tubing which transitions from a single elongated hollow member 10 to a plurality of flexible, hollow infusion arms 26 which are also comprised of a flexible polymer material. A leading flexible tip 55 is positioned distally of the infusion segment. Nitinol or other shape memory metal wire support elements 27 extend through each lumen 25 of the hollow infusion arms 26. Support elements 27 are pre-formed into an expanded infusion segment profile so that when the constraining sleeve or catheter is retracted as previously described, the infusion segment expands to the pre-formed profile as shown in FIG. 3. As shown in Detail A-A of FIG. 3, support elements 27 are positioned within the lumens 25 of infusion arms 26, which are coaxially surrounded by and held in position by the proximal collar 40. The support elements 27 may be formed of solid shape memory wire elements, or they can be formed by longitudinally cutting a metal cannula to form support elements with a wedge-shaped cross-sectional profile as shown in Detail A-A. The support elements 27 may be free-floating within the lumens 25 of the arms 26 or alternatively, the elements 27 may be positioned within the wall of the infusion arms 26.

In operation, the fluid delivery system 1 is inserted into the vasculature and advanced to the treatment site using the leading flexible tip 55 to facilitate advancement through the vessel. Once positioned, the restraining sleeve or catheter is retracted which causes the infusion segment 20 to expand radially outward as the individual support elements 27 "spring" into their unrestrained, preformed shapes as shown in FIG. 3. Fluid delivered through the catheter shaft lumen 10 advances through the infusion arms 26 and exits into the targeted tissue via infusion port slits 63, as described in more detail below.

The polymer shaft embodiment of the infusion device of the current invention is advantageous in several respects.

This embodiment may be designed to be larger to treat larger vessels or ducts. In this embodiment, a device as large as 20 French may be used to treat thrombus or other diseases in larger vessels and ducts. Smaller embodiments may be used to clear thrombus buildup within implanted medical devices such as dialysis catheters or grafts. Additionally, the device may be used to deliver antibacterial or other treatment drugs to vascular access implants such as central or peripheral catheters. The flexibility of the device provides a non-traumatic, exterior surface which will not damage or otherwise compromise the implanted device when clearing intraluminal obstructions. Using flexible material to coaxially surround the pre-formed support elements enhances the overall structural integrity of the device. In addition, the use of a polymer material allows a greater range of design choices with regarding to the infusion ports as will be described in greater detail with reference to FIG. 6A-6D.

Figure 4:
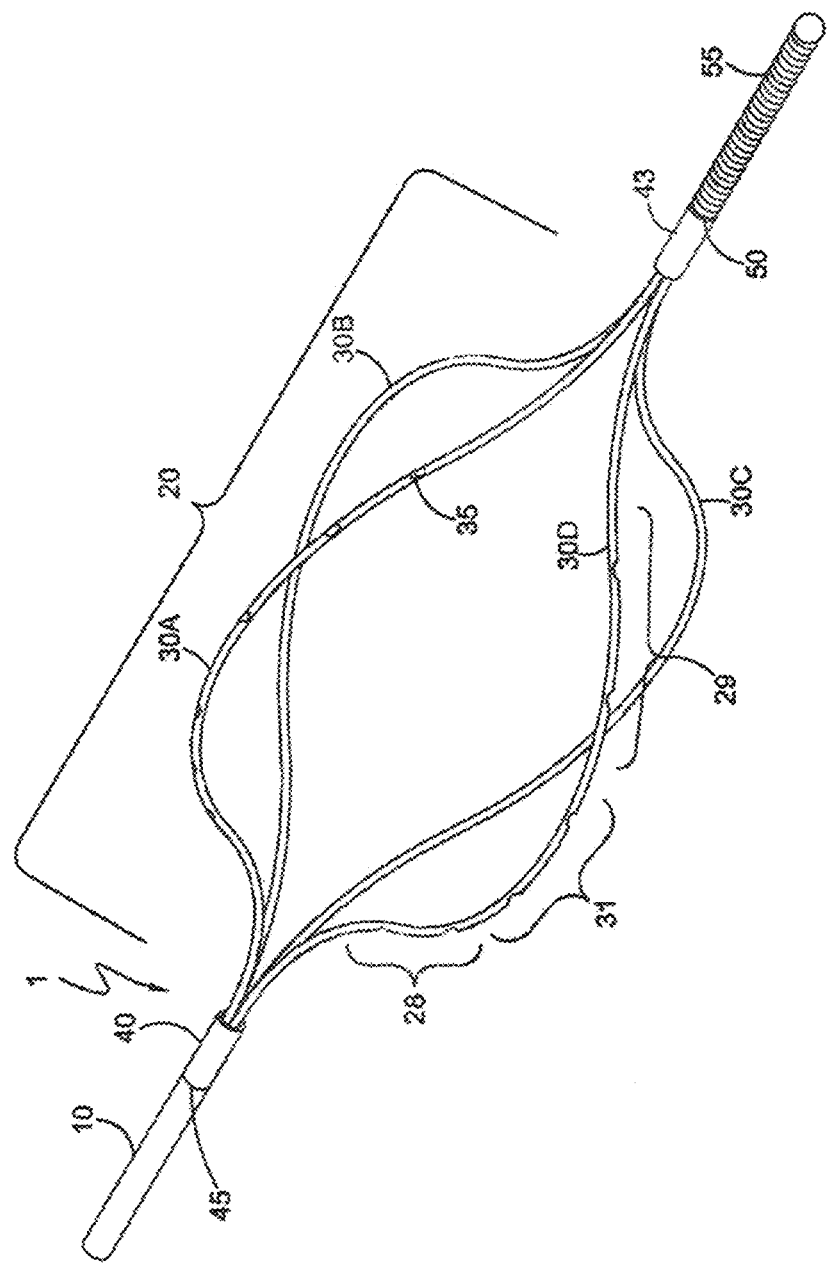
FIG. 4 is an isometric view of the distal section of the fluid delivery device illustrating an embodiment of the infusion segment.

Referring now to FIG. 4, an isometric enlarged view of the distal section of device 1 is shown. The elongated hollow member 10 terminates at the proximal collar 40 from which four tubular infusion arms 30A-30D emerge. In one embodiment, the outer diameter of the elongated hollow member 10 is approximately 0.035" with each infusion arm 30A-D being approximately 0.010-0.012". The internal lumen of each infusion arm may be approximately 0.005-0.008". The infusion arms 30A-D expand outwardly at radial segment 28, then transition to a maximum outer diameter at segment 31 before turning radially inward along segment 29. In one embodiment, the infusion arms 30A-D expand to a maximum diameter of 13-19 mm.

The embodiment of FIG. 4 is designed to allow the infusion device to be inserted through the lumen of an interventional device. As an example, the operator may insert the device of the current invention through the lumen of a standard angioplasty device after the initial angioplasty procedure has been completed. The device may be advanced through the end hole of the angioplasty catheter and positioned within the previously treated vessel segment. The infusion segment of the device may then be expanded so as to contact the treated wall. Once positioned, fluid may be delivered to the treated site through the plurality of infusion exits. As an example, restenosis inhibiting agents known in the art may be delivered directly to the treated area through the infusion device. Thus in another aspect of the current invention, the infusion device described herein may be used to provide an adjunctive therapy during a single treatment procedure.

Figure 5:
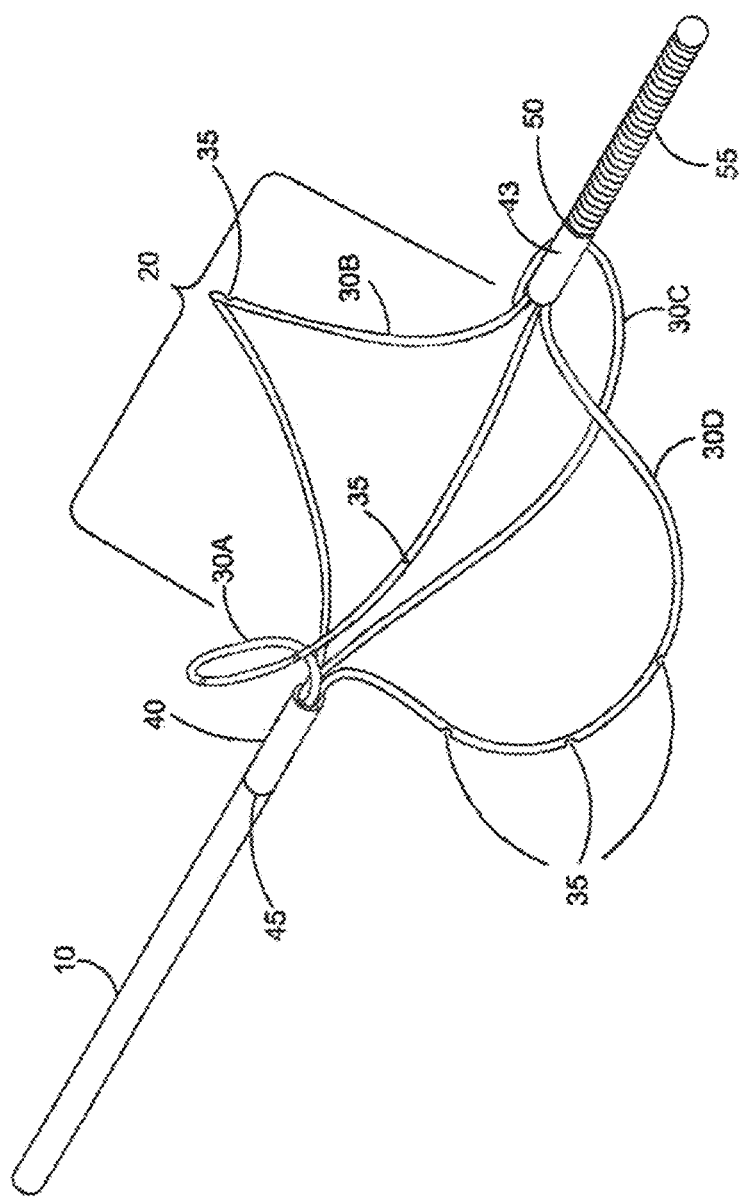
FIG. 5 is an isometric view of the distal section of the fluid delivery device illustrating an embodiment of the infusion segment with twisted infusion arms.

FIG. 5 illustrates an isometric view of yet another embodiment of the current invention. In this embodiment, the individual infusion arms 30A-30D are pre-formed to form a twist-shaped infusion segment basket. This embodiment is advantageous when supplementing the drug with mechanical disruption of the clot. The twist shape will aid in the dispersion of the drug along the entire circumference of the inner vessel wall.

The configuration having fluid exit ports positioned along the infusion arms may have several designs as shown in FIG. 6A-6D. The fluid infusion ports 35 can be in the shape of holes 62 as shown in FIG. 6A, slits 63 as in 6B, or various skive designs as shown in FIG. 6C and FIG. 6D. There can be either a single fluid infusion port on each infusion arm 30 or multiple fluid infusion ports on each infusion arm 30 as in FIG. 6A-6D. The fluid infusion ports can be oriented on an inner surface of the infusion arms 30 pointed towards the inner periphery of the expandable infusion segment to direct drugs such as clot dissolving agents towards a clot located within the lumen of a vessel. Alternatively, the fluid infusion ports can be oriented to outer surface of the infusion arms 30 pointed towards the outer periphery of the expandable infusion segment to maximize fluid contact with the inner vessel wall. The slits 63 as seen in FIG. 6B can be used with the polymer embodiment, which is described in further detail below.

As shown in FIG. 6A, a plurality of holes 62 is are positioned along infusion arm 30. Holes 62 may be formed using drilling, laser, electrical-discharge machining (EDM) or punch techniques known in the art. The hole diameter may be adjusted so as to control the rate at which the fluid exits the device. For example, the smaller the holes, the higher the velocity at which the fluid is delivered. The holes may also be positioned in a pattern which optimizes dispersion of the fluid along the entire infusion segment.

Referring now the embodiment shown in FIG. 6B, a series of infusion ports 35 are in the form of pressure responsive slits 63 which evenly distribute fluid along the entire infusion length of each arm. The slit designs are disclosed in U.S. Pat. Nos. 5,250,034 and 5,267,979, both of which are herein incorporated by reference. These pressure responsive slits 63 are in communication with the lumen of the infusion arms 30 and are designed to open under a predetermined pressure created by the introduction of the fluid agent. This design is particularly suited for a polymer embodiment. The slits 63 also prevent back flow of material into the fluid delivery and treatment device 1. The length of the slits 63 may range from 0.005-0.030" inches in length and may comprise various slit patterns as is known in the art. Patterns having varying fluid infusion port densities and/or lengths are possible on the same infusion arm 30.

In an example of other infusion port embodiments, the fluid infusion ports may be in the shape of skives 64 or 65, as shown in FIGS. 6C-D, which can be used to direct the flow of the fluids in a particular direction. An additional benefit of using infusion ports in the shape of skives 64 or 65 is that the infusion arms 30 will have a sharpened edge at the point where the infusion arms 30 will contact the vessel wall. When the infusion ports are shaped as skives, the infusion segment may be used to simultaneously deliver fluids to the vessel wall while scraping or otherwise abrading the luminal wall. Thus, the skive shapes facilitate and enhance the treatment of various conditions. For example, rotation of the device may cause the skives to scrape a stenotic lesion within a vessel. The collapse of a lumen due to mechanical abrasion of the vessel wall may be achieved by the sharp edges of the skived holes. Mechanical abrasion of the wall may be done prior to, during, or after the delivery of fluids, depending on the medical condition being treated.

The skives 64 or 65 may further be used to achieve the mechanical disruption of a thrombus within a native vessel/graft or implant lumen. The skives may also be used to cause disruption of loculated abscesses to improve complex drainage procedures. With this method, the device of the current invention may be inserted into and through the lumen of a drainage catheter. The device may then be used to deliver antibiotic or other fluid, after which the infusion segment may be rotated to disrupt or break up loculations within the abscess. In another example, the device may be used to supplement tumor treatment by the delivery of chemotherapeutic or ablative agents (such as alcohol) to the targeted tumor. Alternatively, conductive fluid such as saline may be delivered to the tumor volume prior to or during the delivery of either thermal energy or non-thermal electrical pulses to achieve irreversible electroporation, as is known in the art. In yet another embodiment of the method of this invention, the device may be designed so as to deliver occlusion agents and/or abrasive action to fallopian tubes for closure.

Figure 7A:
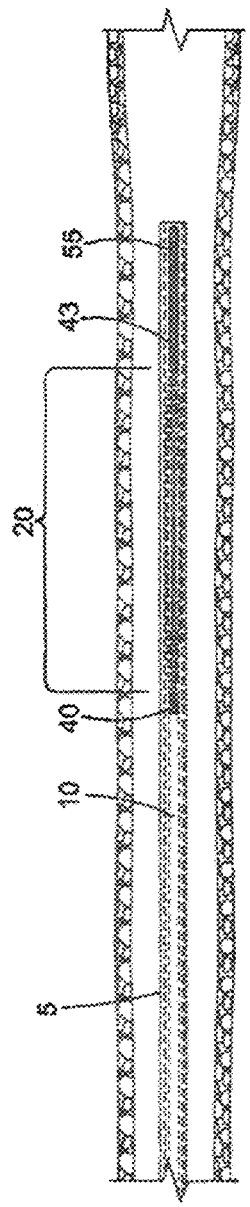
Figure 7B:
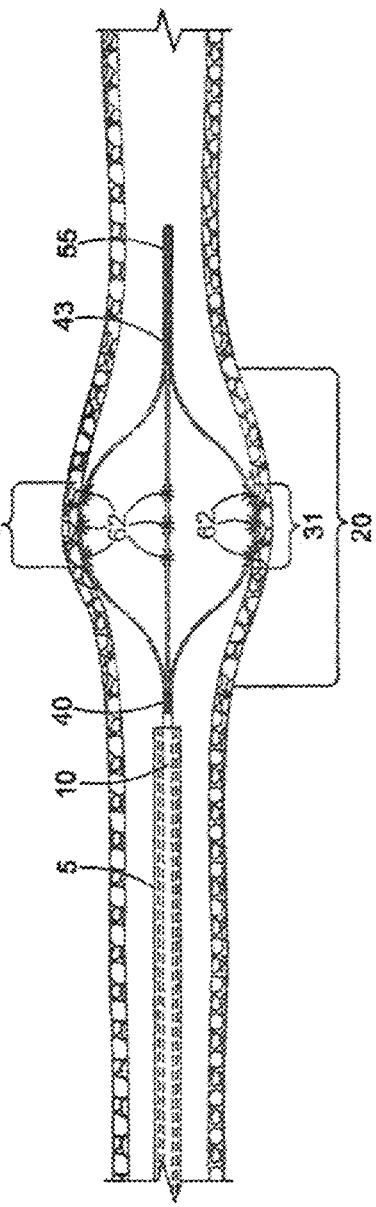

FIGS. 7A-7B illustrate one method of using the device of the current invention. In FIG. 7A, the device 1 is shown already advanced to the target treatment site. In one embodiment, the device 1 will fit within the lumen of a procedure catheter or sheath 5. When the device 1 is within the lumen of the procedure sheath, the expandable infusion segment 20 is in a collapsed or compressed position. As seen in FIG. 7B, the procedure sheath 5 may be retracted proximally so that the entire expandable infusion segment 20 is fully exposed and expanded. After the expandable infusion segment 20 has fully expanded and is in contact with the vessel wall 31, the device is ready to deliver the intended fluids and/or provide mechanical treatment, as previously described.

Figure 7E:
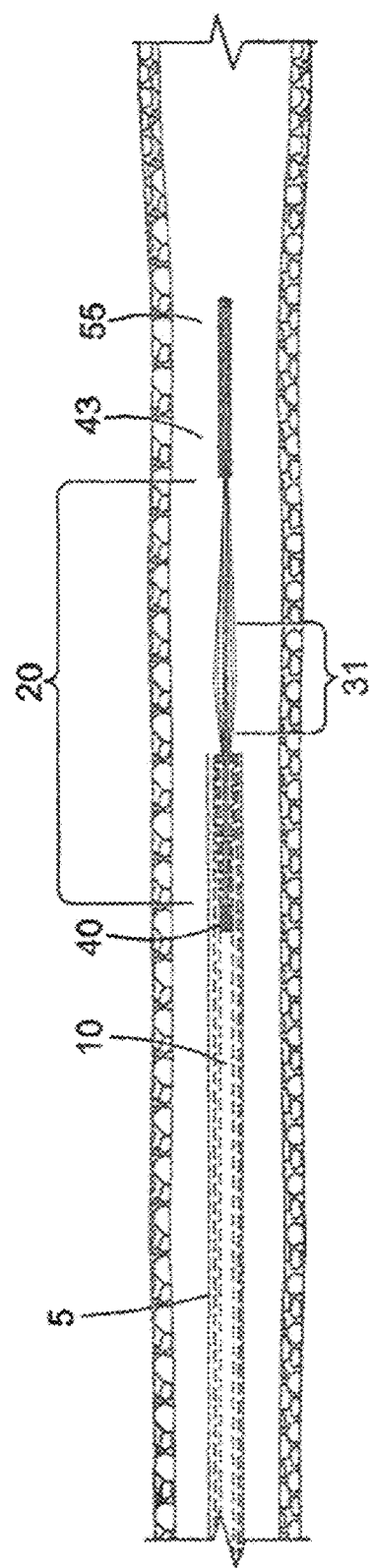

Alternatively, as shown in FIG. 7E, the procedure sheath 5 can be partially retracted so that the profile or diameter of the expandable infusion segment 20 is less than the profile at full expansion. Further, while the expandable infusion segment is only partially expanded, one or more holes may be exposed, allowing for the infusion of liquid drugs. This may be particularly desirable when the user wants to infuse drugs to the inner core of a thrombus mass. Alternatively, partial expansion of the expandable infusion segment 20 can be achieved through the use of a tension wire. For example, the tension wire may extend from the hub 16 to a distal portion of the infusion segment, such as the distal collar 43 where it may be secured. In this fashion, the tension wire may be used to adjust the deployment profile of the infusion segment. The user may then mechanically expand the infusion segment to a desired diameter before infusing fluid.

FIG. 7C and FIG. 7D illustrate a method of treating a thrombus 134 using an infusion device as previously described, an expandable capture sheath 125 and a procedure sheath 5. The expandable capture sheath 125 consists of an elongate shaft 110 having an expandable cone member 120 disposed at a distal end thereof. The expandable capture sheath 125 can be positioned over the infusion device when within the lumen of the procedure sheath 5. The elongate shaft 110 is sized to be disposed within and move independently of both the procedural sheath 5 and the elongated hollow member 10. The expandable sheath 125 is designed to collect and capture the thrombus and thrombus debris for removal from the vessel.

The elongated shaft 110 can be made of materials similar to those of the elongated hollow member 10, as described above. The expandable cone member 120 can be made from a plurality of Nitinol wire members 122 encased with a material 123 bonded thereto. Permeability of the material 123 can facilitate the maintenance of blood flow, however permeability of the material 123 is optional. In a preferred embodiment, the expandable cone member 120 is shaped like a funnel. The Nitinol wire members 122 can be covered with an impervious material 123 or formed as a tight mesh so that the expandable cone member 120 can capture smaller pieces of thrombus debris.

Each wire member 122 of the expandable cone member 120 includes a proximal end 126 and distal end 128. Adjacent proximal ends may come together and be welded or bonded to elongate shaft 110 using an epoxy. Adjacent distal ends 128 form a leading edge defining an open mouth 132 of expandable cone member 120. The expandable cone member 120 can also be made from a wire mesh encased with a permeable material bonded thereto.

When in use, the expandable cone member 120 is collapsed within a procedure sheath 5 and the expandable infusion segment 20 is collapsed within the elongated shaft 110 of the expandable cone member 120 (not shown). The expandable infusion segment 20 is moved into position either distally of the thrombus as shown in FIG. 7C, or within the clot as shown in FIG. 7D. The expandable cone member 120 is advanced distally to the thrombus 134 while the expandable infusion segment 20 is held stationary. Alternatively, the procedure sheath 5 can be proximally retracted, allowing the expandable cone member 120 to self-expand or be mechanically expanded.

Now with reference to FIG. 7D, the infusion device delivers fluids to the site of the thrombus 134 along its outer most portions using an intended drug for softening the clot and preparing it for removal. To supplement the drug's lysis action, the expandable infusion segment 20 may be manipulated as previously described to further disrupt and abrade the thrombus through mechanical action. The softened thrombus 134 and any fragmented thrombus debris 135 or emboli may be dragged into the expandable cone member 120 by retracting the expandable infusion segment 20. Alternatively, the expandable infusion segment 20 can be used to hold the thrombus 134 stationary while distally advancing the expandable cone member 120 to capture the thrombus 134. Once the softened thrombus 134 and any softened thrombus debris 135 has been captured within the expandable cone member 120, the expandable infusion segment 20 and expandable sheath 125 may be retained by the procedural sheath 5 for removal. Additionally, removal of the thrombus 134 and any thrombus debris 135 may be facilitated using standard aspiration techniques. Clot fragments can be aspirated into an annular space between the outer wall or shaft 10 and the inner wall or shaft 110 and out of the hub.

Figure 8:
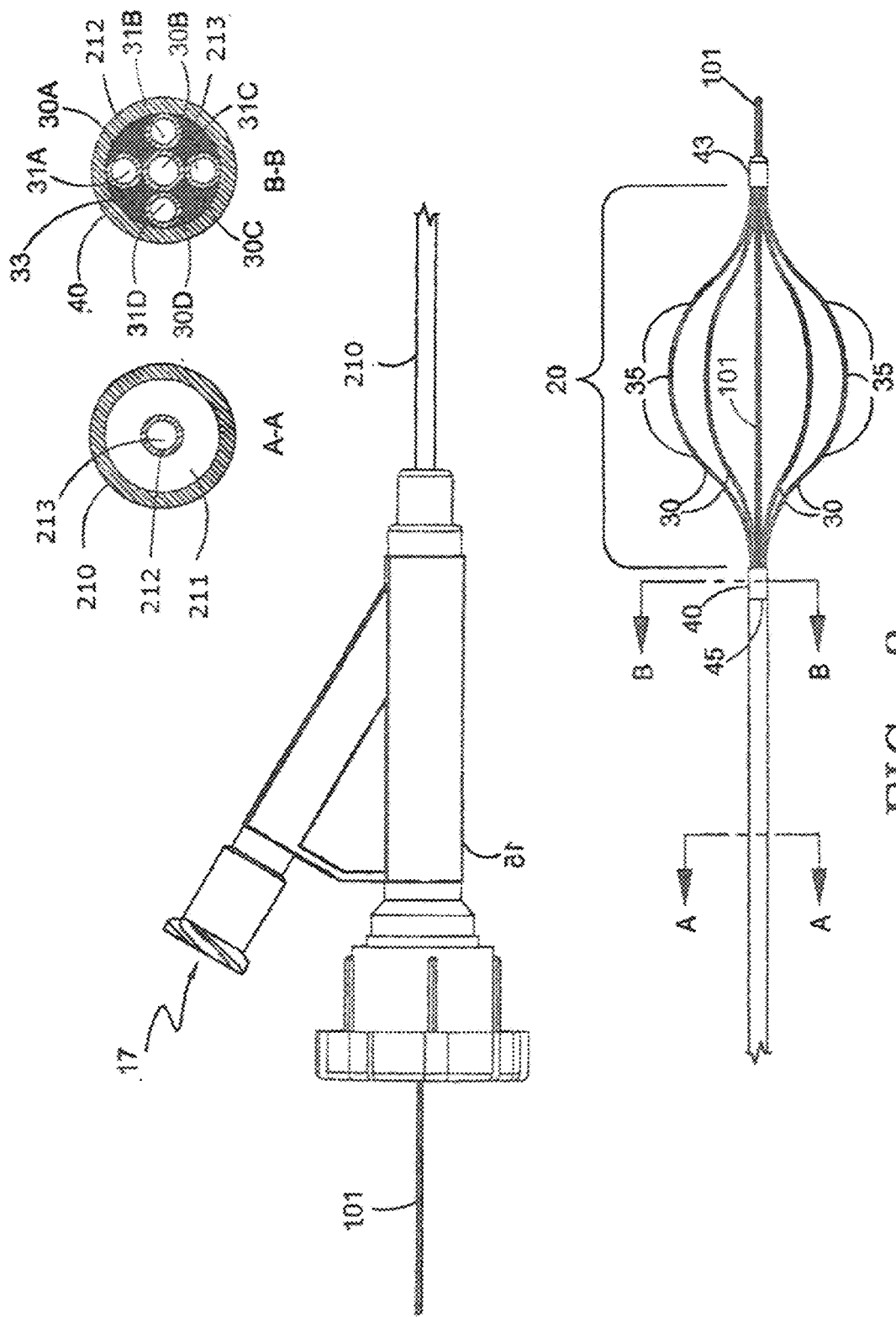
FIG. 8 is a partial plan view of an embodiment of the fluid delivery device designed to be advanced over a standard guidewire.

FIG. 8 illustrates another embodiment of the infusion device designed to be used with a standard guidewire. The leading flexible tip 55 of FIG. 1 has been replaced with a distal tip section having a through lumen which allows the entire device to be backloaded over a standard guidewire 101. The elongated hollow member 210 extends from Y-connector 15 distally to the expandable infusion segment 20. As shown in cross-section A-A of FIG. 8, within lumen 211 of elongated hollow member 210 is a dedicated guidewire lumen 213 which extends distally from the Y-connector and terminates at the distal edge of the proximal collar 40. The side arm port 17 is in fluid communication with the lumen 211 of the elongated hollow member 210, providing a fluid path from the Y-arm of the connector 15 to the infusion arm lumens 31A-31D. As shown in "B-B", the dedicated guidewire lumen 213 is coaxially surrounded by infusion arms 30A-30D. The proximal collar 40 coaxially surrounds the guidwire lumen 213 and infusion arms 30A-D. The Y-connector 15 may include a Touhy-Borst assembly, which is a gasket assembly used for holding and sealing around guidewires or other interventional devices. The guidewire compatible design shown in FIG. 8 may be sized to be used with guidewires of various sizes ranging from 0.014"-0.045".

In an alternative embodiment the coaxially-positioned guidewire tube 212 may extend distally from the distal most end of the proximal collar 40 to the distal end of distal collar 43. Lumen 213 of guidewire tube 212 provides a pathway for the guidewire along the entire length of the device.

In operation, the device of FIG. 8 is loaded over a guidewire by first collapsing the device infusion segment inside an insertion tool (tube) and then threading the proximal most end of guidewire 101 into the distal end hole of the device at distal collar 43. The guidewire 101 is advanced until it exits Y-connector 15, as shown in FIG. 8. The insertion tool can then be used to insert the collapsed distal infusion segment through the hub of a procedural catheter or sheath. Alternatively, the guidewire is placed in the vessel and positioned at the target area, then the device is threaded over the guidewire. The device is then advanced over the guidewire to the target area.

Figure 11:
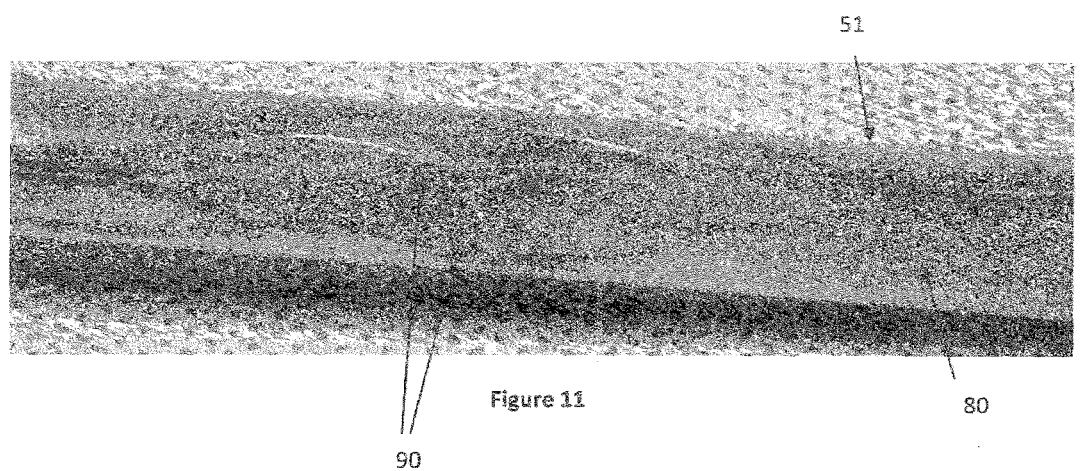
FIG. 11 is a photographic image of the prototype of FIG. 9 positioned within a gel-filled tube illustrating fluid dispersion into the gel mass.

FIGS. 9-11 are photographic images of one embodiment of the current invention. FIG. 9 shows the distal portion of the device 1 with the infusion segment 20 in an expanded or deployed position. The sleeve/catheter 5 is shown retracted proximally away from the infusion segment. Four infusion arms 30 are shown in a twist configuration. The proximal collar 40 is attached to the device shaft 10 and the distal collar 43 is attached to leading flexible tip 55. FIG. 10 is a photographic image of the device of FIG. 9 shown with fluid 50 exiting the plurality of exit ports at a high velocity. FIG. 11 illustrates the dispersion of the red-colored fluid 90 within a gel-filled tube 51. As shown, the injected red fluid 90 is dispersed throughout the green gel along the infusion segment length and extending outwardly to the tube 51 wall.

Figure 12:
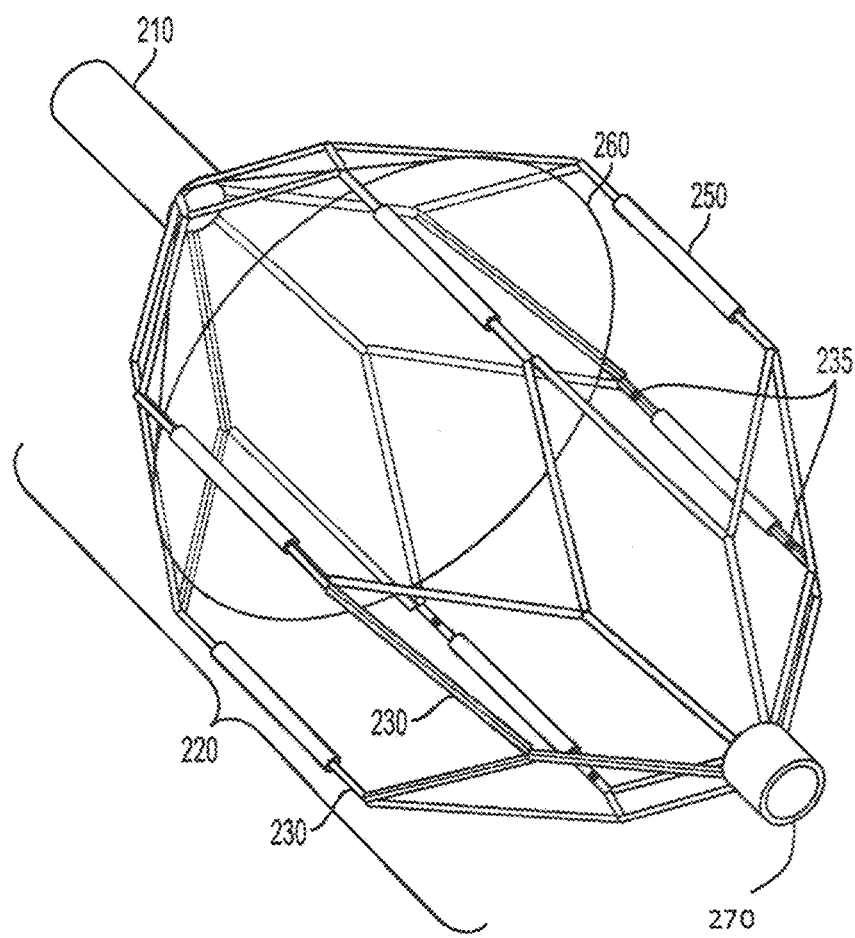
FIG. 12 is an isometric view of an embodiment of an expandable segment having rollers.

FIG. 12 illustrates an alternate embodiment of an expandable segment 220. In this embodiment, the device comprises an expandable segment 220 that has rollers 250 on the expandable arms 230 of the expandable segment. The outer portion of the expandable segment 220 can contain one or more roller 250. The expandable arms 230 can be made from Nitinol or other materials as described for the infusion segment above, and the rollers 250 can be made of Teflon tubing or some other non-stick biocompatible material. The expandable segment 220 may also have one or more straight expandable arm segments 230 to accommodate the geometry of a tubular shaped roller 250. Turning or rotating the expandable segment 220 within or around the clot would cause mechanical disruption of the clot to so that the clot becomes dislodged from the vessel and fragments into smaller masses. Further, using rollers 250 on the outer edges of the expandable segment 220 helps to prevent the vessel from twisting while the expandable segment 220 is being rotated. Alternatively, the expandable arms 230 may contain a hydrophilic coating to enhance movement across the vessel wall surface. This aids in preventing the expandable segment 220 from binding or catching on to the inner vessel wall, causing the vessel to twist.

The proximal end of the expandable segment 220 may contain a filter 260 for catching clot debris. The filter 260 can also be used for trapping clot debris or the entire clot for removal as the expandable segment 220 is retracted into a procedure sheath. The distal end of the expandable segment 220 can be configured to mechanically and physically break up, dislodge or remove the clot by rotating the expandable segment 220. For example, the expandable arms 230 on the distal end of the expandable segment 220 may be shaped with sharpened edges or skive shaped elements for breaking up a clot. Alternatively, since the expandable segment 220 is self-centering within the vessel, the distal-most tip 270 of the expandable segment 220 may include a corkscrew shaped element (not shown) to help in breaking up a clot.

In an alternative embodiment, the expandable segment 220 can be either self-expanding or expanded by mechanical means, such as a tension wire as described above. Infusion ports 235 could also be located on the expandable arms 230 to allow for the infusion of fluid into the vessel. Alternatively, expandable arms 230 may include a flexible polymer tubing for infusing fluid into the vessel as described above.

The fluid delivery and treatment device 1 is designed to be used in a variety of body lumens, including but not limited to veins, arteries, ducts, brachial tubes, esophagus, or any other vessel that requires the delivery of drugs or fluids. The device can be used to deliver a variety of medical preparations including therapeutic agents and diagnostic agents for therapeutic or diagnostic purposes.

The invention claimed is:

1. A method of treating a thrombus mass within a human vessel, comprising:
   inserting a treatment device into the human vessel, the treatment device comprising a procedure sheath, an expandable infusion segment, and an expandable capture sheath,
      wherein the expandable infusion segment comprises a plurality of expandable arms and a plurality of fluid channels, each of the plurality of expandable arms further include flexible polymer tubing and at least one pressure responsive infusion port,
      wherein each of the plurality of expandable arms contain at least one support element made from a memory shape metal and extends co-axially along each of the plurality of fluid channels, the at least one support element has a first shape and a second shape, the first shape being closer to a longitudinal axis of the expandable infusion segment than the second shape, and
      wherein at least one of the plurality of fluid channels is in fluid communication with the at least one pressure responsive infusion port, the at least one pressure responsive infusion port designed to open under a predetermined pressure;
   inserting the treatment device through an outer sheath, the at least one support element being in the first shape when the outer sheath is in a position toward a distal end of the treatment device and the at least one support element automatically expanding to the second shape when the outer sheath is moved toward a proximal end of the treatment device;
   advancing the expandable infusion segment to the thrombus mass;
   delivering a first amount of fluid through the at least one pressure responsive infusion port to a site of the thrombus mass while the expandable infusion segment is at a first diameter;
   manipulating the expandable infusion segment to mechanically disrupt the thrombus mass, the expandable infusion segment contacting the thrombus mass to disrupt and separate the thrombus mass from a vessel wall after delivering the first amount of fluid; and
   retracting the expandable infusion segment in a proximal direction, the expandable infusion segment bringing the thrombus mass into the expandable capture sheath for removal of the thrombus mass from the vessel.

2. The method of claim 1, further comprising:
   positioning the expandable capture sheath proximate to the expandable infusion segment and the thrombus mass.

3. The method of claim 2, further comprising:
   advancing the expandable capture sheath towards the thrombus mass.

4. The method of claim 2, further comprising:
   manipulating the expandable capture sheath to mechanically abrade the thrombus mass.

5. The method of claim 2, further comprising:
   retracting the expandable infusion segment into the expandable capture sheath to capture at least a portion of the thrombus mass into the expandable capture sheath.

6. The method of claim 2, further comprising:
aspirating at least a portion of the thrombus mass through a space formed at least partially by the expandable capture sheath.

7. The method of claim 1, wherein the at least one pressure responsive infusion port is formed to direct a flow of fluid, further comprising:
directing fluid exiting the at least one pressure responsive infusion port in a direction substantially along the longitudinal axis of the expandable infusion segment.

8. The method of claim 1 further comprising:
delivering fluid to an inner core of the thrombus mass.

9. The method of claim 1 further comprising:
delivering fluid to an outer periphery of the thrombus mass.

10. A method of treating a thrombus mass within a human vessel, comprising:
inserting a treatment device into the human vessel, the treatment device comprising a procedure sheath, an expandable infusion segment, and an expandable cone member,
wherein the expandable infusion segment comprises a plurality of expandable arms and a plurality of fluid channels, each of the plurality of expandable arms further include flexible polymer tubing and at least one pressure responsive infusion port,
wherein each of the plurality of expandable arms contain at least one support element made from a memory shape metal and extends co-axially along each of the plurality of fluid channels, the at least one support element has a first shape and a second shape, the first shape being closer to a longitudinal axis than the second shape, and
wherein at least one of the plurality of fluid channels is in fluid communication with the at least one pressure responsive infusion port, the at least one pressure responsive infusion port has a first position and a second position, the at least one pressure responsive infusion port being closed at the first position and open at the second position;
inserting the treatment device through an outer sheath, the at least one support element being in the first shape when the outer sheath is in a position toward a distal end of the treatment device and the at least one support element automatically expanding to the second shape when the outer sheath is moved toward a proximal end of the treatment device;
advancing the expandable infusion segment to the thrombus mass;
delivering a first amount of fluid through at least one pressure responsive infusion port to a site of the thrombus mass while the expandable infusion segment is at a first diameter, the delivering of the first amount of fluid forcing the at least one pressure responsive infusion port from the first position to the second position;
manipulating the expandable infusion segment to mechanically disrupt the thrombus mass, the expandable infusion segment contacting the thrombus mass to disrupt and separate the thrombus mass from a vessel wall after delivering the first amount of fluid; and
retracting the expandable infusion segment in a proximal direction, the expandable infusion segment bringing the thrombus mass into the expandable cone member for removal of the thrombus mass from the vessel.

* * * * *